(12) United States Patent
Luo et al.

(10) Patent No.: US 11,047,233 B2
(45) Date of Patent: Jun. 29, 2021

(54) IDENTIFYING HYDROCARBON SWEET SPOTS USING CARBON DIOXIDE GEOCHEMISTRY

(71) Applicant: SAUDI ARABIAN OIL COMPANY, Dhahran (SA)

(72) Inventors: Pan Luo, Dhahran (SA); Peng Lu, Dhahran (SA); Khaled Arouri, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/553,930

(22) Filed: Aug. 28, 2019

(65) Prior Publication Data

US 2021/0062649 A1  Mar. 4, 2021

(51) Int. Cl.
  *E21B 49/08* (2006.01)
  *E21B 49/00* (2006.01)
  *G01N 33/24* (2006.01)

(52) U.S. Cl.
  CPC .......... *E21B 49/082* (2013.01); *E21B 49/003* (2013.01); *G01N 33/241* (2013.01); *E21B 49/0875* (2020.05)

(58) Field of Classification Search
  CPC .... G01N 33/241; E21B 49/003; E21B 49/082
  See application file for complete search history.

(56) References Cited

U.S. PATENT DOCUMENTS 3,571,591 A * 3/1971 Bradley .................. G21H 5/02
                                                    250/255
3,645,131 A    2/1972 Turner et al.
(Continued)

FOREIGN PATENT DOCUMENTS

AU    2008201132 A1    10/2008

OTHER PUBLICATIONS

Courel et al., "Identifying and Assessing Productivity in CO2 Bearing Gas Zones Using Wireline Logging and Testing Data", OTC held in Kuala Lumpur, Malaysia, 2014, pp. 21, Offshore Technology Conference.

(Continued)

*Primary Examiner* — John Fitzgerald (74) *Attorney, Agent, or Firm* — Bracewell LLP; Constance G. Rhebergen (57) ABSTRACT

Embodiments provide a method for evaluating a hydrocarbon-bearing formation. The method includes the step of identifying a hydrocarbon sweet spot. The identifying step includes determining a carbon dioxide content of a gas sample retrieved from the hydrocarbon-bearing formation. The identifying step includes determining an isotopic signature of carbon dioxide of the gas sample. The carbon dioxide content of the gas sample retrieved from the hydrocarbon sweet spot can have a mole percentage ranging from 9 percent to 20 percent. The isotopic signature of carbon dioxide of the gas sample retrieved from the hydrocarbon sweet spot can have a $\delta^{13}C$ value greater than $-10$ per mil. The identifying step can further include determining a cutoff range of the carbon dioxide content corresponding to the hydrocarbon sweet spot. The cutoff range can have a mole percentage ranging from 9 percent to 20 percent. The identifying step can further include obtaining a gas flow rate of the hydrocarbon-bearing formation. The gas flow rate can be greater than 10 million standard cubic feet per day.

8 Claims, 8 Drawing Sheets

(56) References Cited

U.S. PATENT DOCUMENTS

| | | | | |
|---|---|---|---|---|
| 3,649,201 | A | * | 3/1972 | Scalan ................ G01N 33/241 436/27 |
| 4,340,391 | A | * | 7/1982 | Demaison ............. G01V 9/007 436/29 |
| 4,517,461 | A | * | 5/1985 | Crandall ................ B01D 59/44 250/281 |
| 5,328,849 | A | * | 7/1994 | Smith ................ G01N 33/241 436/32 |
| 5,416,024 | A | * | 5/1995 | Smith ................ G01N 33/241 436/32 |
| 7,210,342 | B1 | * | 5/2007 | Sterner ................ E21B 21/01 73/152.18 |
| 7,395,691 | B2 | | 7/2008 | Sterner et al. |
| 8,445,841 | B2 | | 5/2013 | Szobota et al. |
| 8,714,246 | B2 | | 5/2014 | Pop et al. |
| 8,899,348 | B2 | | 12/2014 | Henderson et al. |
| 9,128,076 | B2 | * | 9/2015 | Lamberti ............. G01N 33/241 |
| 9,470,068 | B2 | | 10/2016 | Kacewicz |
| 9,546,959 | B2 | | 1/2017 | Indo et al. |
| 9,890,617 | B2 | * | 2/2018 | Lawson ................ E21B 43/00 |
| 10,031,024 | B2 | | 7/2018 | Pope et al. |
| 10,094,815 | B2 | * | 10/2018 | Lawson ................ G01V 9/007 |
| 10,400,596 | B2 | * | 9/2019 | Lawson ............... G01N 33/241 |
| 10,415,379 | B2 | * | 9/2019 | Lawson ................ E21B 47/07 |
| 10,494,923 | B2 | * | 12/2019 | Lawson ................ G01V 9/007 |
| 10,533,414 | B2 | * | 1/2020 | Lawson ................ G01V 9/007 |
| 2008/0147326 | A1 | * | 6/2008 | Ellis ........................ G01V 9/007 702/9 |
| 2011/0030465 | A1 | * | 2/2011 | Smalley ................ E21B 47/11 73/152.07 |
| 2011/0250582 | A1 | | 10/2011 | Gates et al. |
| 2012/0053838 | A1 | * | 3/2012 | Andrews ............... E21B 49/082 702/8 |
| 2014/0284465 | A1 | * | 9/2014 | Pottorf .................... G01N 1/00 250/253 |
| 2014/0288853 | A1 | * | 9/2014 | Dreyfus .................. G01N 1/00 702/27 |
| 2015/0127313 | A1 | * | 5/2015 | Lawson ................ E21B 43/16 703/10 |
| 2015/0167445 | A1 | | 6/2015 | Pirolli et al. |
| 2016/0084045 | A1 | * | 3/2016 | Lawson ............... G01V 99/005 703/10 |
| 2016/0084817 | A1 | * | 3/2016 | Lawson ............... G01N 33/241 702/6 |
| 2016/0177711 | A1 | * | 6/2016 | Calleri ................ G01N 33/241 73/152.04 |
| 2016/0222781 | A1 | * | 8/2016 | Lawson ............... G01N 33/241 |
| 2016/0222782 | A1 | * | 8/2016 | Lawson ................ G01V 9/007 |
| 2016/0258922 | A1 | * | 9/2016 | Formolo ................ E21B 49/00 |
| 2017/0002630 | A1 | * | 1/2017 | Priezzhev ............ G06F 16/245 |
| 2017/0226851 | A1 | * | 8/2017 | Hakami ................ E21B 47/07 |
| 2018/0313807 | A1 | * | 11/2018 | Michael ................ E21B 43/30 |
| 2018/0321215 | A1 | * | 11/2018 | Peterson ................ E21B 47/11 |
| 2019/0048717 | A1 | * | 2/2019 | Lu ........................ G01N 33/241 |
| 2019/0055842 | A1 | * | 2/2019 | Lu ........................ G01V 11/005 |

OTHER PUBLICATIONS

Dai et al., "Geochemistry and Accumulation of Carbon Dioxide Gases in China", AAPG Bulletin, 1996, pp. 1615-1626, vol. 80, No. 10, The American Association of Petroleum Geologists.

Deng et al., "Petrophysics of Triple-Porosity Tight Gas Reservoirs With a Link to Gas Productivity", SPE Reservoir Evaluation & Engineering, 2011, pp. 566-577, Society of Petroleum Engineers.

Fleet et al., "Large volumes of carbon dioxide in sedimentary basins", Mineralogical Magazine, 1998, pp. 460-461.

Franks et al., "Relationships Among Secondary Porosity, Pore-Fluid Chemistry and Carbon Dioxide, Texas Gulf Coast", Concepts and Principles, 1984, pp. 63-79.

Luo et al., "CO2 Indicators for Sweet Spots in Tight Formations, North West Saudi Arabia", AAPG/SEG International Conference and Exhibition, England, Presentation, 2017, pp. 19.

Meckel et al., "Pervasive Tight—Gas Sandstone Reservoirs: An Overview", AAPG Hedberg Series, 2008, pp. 13-27, No. 3, The American Association of Petroleum Geologists.

Ronald C. Surdam, "A New Paradigm for Gas Exploration in Anomalously Pressured "Tight Gas Sands" in the Rocky Mountain Laramide Basins", AAPG Memoir 67, 1997, pp. 283-298.

Shanley et al., "Factors controlling prolific gas production from low-permeability sandstone reservoirs: Implications for resource assessment, prospect development, and risk analysis", AAPG Bulletin, 2004, pp. 1083-1121, The AAPG.

International Search Report and Written Opinion of PCT Application No. PCT/US2020/048529 dated Dec. 21, 2021: pp. 1-16.

Estarabadi et al., "The Application of Well Site Isotopic Analysis for Reservoir Evaluation," SPWLA 57th Annual Logging Symposium, Society of Petrophysicists and Well Log Analysis, Jun. 2016: pp. 1-13.

Guang et al., "Formation of carbon dioxide and hydrocarbon as reservoirs in the Changling fault depression, Songliao Basin," Petrol. Explor. Develop., vol. 38(1), Feb. 2011: pp. 52-58.

* cited by examiner

IDENTIFYING HYDROCARBON SWEET SPOTS USING CARBON DIOXIDE GEOCHEMISTRY

BACKGROUND

Field of the Disclosure

Embodiments of the disclosure generally relate to identifying hydrocarbon sweet spots. More specifically, embodiments of the disclosure relate to methods for identifying hydrocarbon sweet spots in hydrocarbon-bearing formations using carbon dioxide geochemistry.

Description of the Related Art

Carbon dioxide ($CO_2$) is a common non-hydrocarbon component associated with oil and natural gas. It exists in subterranean regions worldwide in a variety of geological settings. The abundance of carbon dioxide trapped in subterranean hydrocarbon-bearing formations (such as tight formations) varies, ranging from trace amounts to the entirety of the produced fluid.

The degree of carbon dioxide abundance in a hydrocarbon-bearing formation is a factor considered during reservoir evaluation, reservoir simulation, field development, and facility design. For example, carbon dioxide content is typically measured in the petroleum industry by implementing gas compositional analysis on fluid samples during formation testing, well testing, reservoir stimulation, and production. The fluid samples are collected using a downhole sampling tool or collected at a wellhead or separator located at the surface.

Measurements of carbon dioxide content are used for various purposes in the petroleum industry. For example, carbon dioxide content data are used as an input for pressure, volume, and temperature (PVT) modelling for reservoir management. Carbon dioxide content data are considered in terms of facility designing to mitigate corrosion due to the dissolved form of carbon dioxide being corrosive against carbon- and steel-based components used for hydrocarbon production. Carbon dioxide content data are considered to reduce carbon dioxide in the produced gas such that the natural gas market requirements are met. Explorationists use certain carbon dioxide geochemical data (such as carbon dioxide content data and carbon isotopic signature data) to track the source and map the distribution of carbon dioxide to avoid drilling a prospect having abundant carbon dioxide. Also, explorationists and reservoir engineers use certain carbon dioxide geochemical data to accurately estimate the hydrocarbon reserve and to predict reservoir compartmentalization.

SUMMARY

Embodiments of the disclosure generally relate to identifying hydrocarbon sweet spots. More specifically, embodiments of the disclosure relate to methods for identifying hydrocarbon sweet spots in hydrocarbon-bearing formations using carbon dioxide geochemistry.

Embodiments of the disclosure provide a method for evaluating a hydrocarbon-bearing formation. The method includes the step of identifying a hydrocarbon sweet spot. The identifying step includes determining a carbon dioxide content of a gas sample retrieved from the hydrocarbon-bearing formation. The identifying step includes determining an isotopic signature of carbon dioxide of the gas sample.

In some embodiments, the carbon dioxide content of the gas sample has a mole percentage ranging from 9 percent (%) to 20%. In some embodiments, the isotopic signature of carbon dioxide of the gas sample has a $\delta^{13}C$ value greater than −10 per mil (‰). In some embodiments, the identifying step further includes determining a cutoff range of the carbon dioxide content corresponding to the hydrocarbon sweet spot. In some embodiments, the cutoff range has a mole percentage ranging from 9% to 20%. In some embodiments, the identifying step further includes obtaining a gas flow rate of the hydrocarbon-bearing formation. In some embodiments, the gas flow rate is greater than 10 million standard cubic feet per day (MMscf/d). In some embodiments, the hydrocarbon-bearing formation is a tight formation. In some embodiments, the gas sample is retrieved via wireline formation testing or drill stem testing.

Embodiments of the disclosure also provide a method for evaluating a hydrocarbon-bearing formation. The method includes the step of identifying a hydrocarbon sweet spot. The identifying step includes determining a carbon dioxide content of a first gas sample retrieved from a pilot well of the hydrocarbon-bearing formation. The identifying step includes determining an isotopic signature of carbon dioxide of the first gas sample. The identifying step includes obtaining a gas flow rate of the pilot well. The identifying step includes determining the carbon dioxide content of a second gas sample retrieved from an appraisal well or a production well.

In some embodiments, the carbon dioxide content of the first gas sample has a mole percentage ranging from 9% to 20%. In some embodiments, the isotopic signature of carbon dioxide of the first gas sample has a $\delta^{13}C$ value greater than −10‰. In some embodiments, the identifying step further includes determining a cutoff range of the carbon dioxide content corresponding to the hydrocarbon sweet spot. In some embodiments, the cutoff range has a mole percentage ranging from 9% to 20%. In some embodiments, the gas flow rate of the pilot well is greater than 10 MMscf/d. In some embodiments, the carbon dioxide content of the second gas sample has a mole percentage ranging from 9% to 20%. In some embodiments, the identifying step further includes determining the isotopic signature of carbon dioxide of the second gas sample. In some embodiments, the isotopic signature of carbon dioxide of the second gas sample has a $\delta^{13}C$ value greater than −10‰. In some embodiments, the hydrocarbon-bearing formation is a tight formation. In some embodiments, the first gas sample is retrieved via wireline formation testing or drill stem testing. In some embodiments, the second gas sample is retrieved via wireline formation testing.

Embodiments of the disclosure also provide a method for producing hydrocarbon from a hydrocarbon-bearing formation. The method includes the step of identifying a hydrocarbon sweet spot by determining a carbon dioxide content of a gas sample retrieved from the hydrocarbon-bearing formation and determining an isotopic signature of carbon dioxide of the gas sample. The method includes the step of producing the hydrocarbon at the hydrocarbon sweet spot.

In some embodiments, the carbon dioxide content of the gas sample has a mole percentage ranging from 9% to 20%. In some embodiments, the isotopic signature of carbon dioxide of the gas sample has a $\delta^{13}C$ value greater than −10‰. In some embodiments, the identifying step further includes determining a cutoff range of the carbon dioxide content corresponding to the hydrocarbon sweet spot. In some embodiments, the cutoff range has a mole percentage ranging from 9% to 20%. In some embodiments, the identifying step includes obtaining a gas flow rate of the hydrocarbon-bearing formation. In some embodiments, the gas flow rate is greater than 10 MMscf/d. In some embodiments, the method further includes the step of stimulating the hydrocarbon-bearing formation. In some embodiments, the hydrocarbon-bearing formation is a tight formation. In some embodiments, the gas sample is retrieved via wireline formation testing or drill stem testing.

BRIEF DESCRIPTION OF THE DRAWINGS

So that the manner in which the previously-recited features, aspects, and advantages of the embodiments of this disclosure as well as others that will become apparent are attained and can be understood in detail, a more particular description of the disclosure briefly summarized previously may be had by reference to the embodiments that are illustrated in the drawings that form a part of this specification. However, it is to be noted that the appended drawings illustrate only certain embodiments of the disclosure and are not to be considered limiting of the disclosure's scope as the disclosure may admit to other equally effective embodiments.

In the accompanying Figures, similar components or features, or both, may have a similar reference label.

DETAILED DESCRIPTION

The disclosure refers to particular features, including process or method steps. Those of skill in the art understand that the disclosure is not limited to or by the description of embodiments given in the specification. The subject matter of the disclosure is not restricted except only in the spirit of the specification and appended claims.

Those of skill in the art also understand that the terminology used for describing particular embodiments does not limit the scope or breadth of the embodiments of the disclosure. In interpreting the specification and appended claims, all terms should be interpreted in the broadest possible manner consistent with the context of each term. All technical and scientific terms used in the specification and appended claims have the same meaning as commonly understood by one of ordinary skill in the art to which this disclosure belongs unless defined otherwise.

Although the disclosure has been described with respect to certain features, it should be understood that the features and embodiments of the features can be combined with other features and embodiments of those features.

Although the disclosure has been described in detail, it should be understood that various changes, substitutions, and alternations can be made without departing from the principle and scope of the disclosure. Accordingly, the scope of the present disclosure should be determined by the following claims and their appropriate legal equivalents.

As used throughout the disclosure, the singular forms "a," "an," and "the" include plural references unless the context clearly indicates otherwise.

As used throughout the disclosure, the word "about" includes +/−5% of the cited magnitude. As used throughout the disclosure, the word "substantial" include +/−10% of the cited magnitude.

As used throughout the disclosure, the words "comprise," "has," "includes," and all other grammatical variations are each intended to have an open, non-limiting meaning that does not exclude additional elements, components or steps. Embodiments of the disclosure may suitably "comprise," "consist," or "consist essentially of" the limiting features disclosed, and may be practiced in the absence of a limiting feature not disclosed. For example, it can be recognized by those skilled in the art that certain steps can be combined into a single step.

As used throughout the disclosure, the words "optional" or "optionally" means that the subsequently described event or circumstances can or may not occur. The description includes instances where the event or circumstance occurs and instances where it does not occur.

Where a range of values is provided in the specification or in the appended claims, it is understood that the interval encompasses each intervening value between the upper limit and the lower limit as well as the upper limit and the lower limit. The disclosure encompasses and bounds smaller ranges of the interval subject to any specific exclusion provided.

Where reference is made in the specification and appended claims to a method comprising two or more defined steps, the defined steps can be carried out in any order or simultaneously except where the context excludes that possibility.

As used throughout the disclosure, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present disclosure.

As used throughout the disclosure, spatial terms described the relative position of an object or a group of objects relative to another object or group of objects. The spatial relationships apply along vertical and horizontal axes. Orientation and relational words, including "downhole" and other like terms, are for descriptive convenience and are not limiting unless otherwise indicated.

As used throughout the disclosure, the term "sweet spot" refers to a target zone, location, or area within a play or a reservoir that represents greater production or potential production relative to zones, locations, or areas other than the target zone, location, or area. Explorationists and reservoir engineers typically map sweet spots such that wellbores are placed in productive or potentially productive areas of the reservoir.

As used throughout the disclosure, the term "tight formation" refers to a relatively impermeable hydrocarbon-bearing formation generally having a permeability of less than about 0.1 millidarcy (mD) and less than about 10% porosity. Non-limiting examples of tight formations include hydrocarbon-bearing sandstone formations, hydrocarbon-bearing limestone formations, and hydrocarbon-bearing shale formations.

As used throughout the disclosure, the term "organic carbon dioxide" refers to carbon dioxide originating from an organic source. Conversely, as used throughout the disclosure, the term "inorganic carbon dioxide" refers to carbon dioxide originating from an inorganic source.

Embodiments of the disclosure provide a use of carbon dioxide geochemistry for exploration and field development. A hydrocarbon sweet spot of a tight formation can be identified based on information related to the content and origin of carbon dioxide. The hydrocarbon sweet spot is representative of enhanced storage capacity (corresponding to porosity) and deliverability (corresponding to permeability) for making decisions to complete a production well.

Carbonate-based minerals are abundant in tight formations. For example, a sandstone formation may include calcite ($CaCO_3$), dolomite ($CaMg(CO_3)_2$), ankerite ($Ca[Fe/Mg/Mn](CO_3)_2$), or siderite ($FeCO_3$). These carbonate-based minerals may serve as cementitious materials or framework grains in sandstones. Carbonates contained in these minerals can be dissolved due to certain changes in the subterranean chemical environment during geological history. For example, carbonates can be dissolved due to organic acid generated from the maturation of organic matter, the injection of carbon dioxide from external sources, the invasion of unsaturated water, increased temperature, or any combination of these factors. Such carbonate dissolution is commonly observed in petrographic analysis and is proposed by certain diagenesis models.

The dissolution of carbonates may result in generating gaseous carbon dioxide as shown in example reactions (1) and (2):

(1)

(2)

Both example reactions (1) and (2) are reversible. Additionally, the dissolution of carbonates (that is, the right-hand side direction of both example reactions (1) and (2)) creates additional pore volume, which is known as secondary porosity. The secondary porosity may connect certain occluded pore throats to increase permeability of the tight formation.

In a tight formation, the generated gaseous carbon dioxide will not escape the formation but may be trapped within. The trapped carbon dioxide results in an increase of formation pressure. The increased formation pressure may function to preserve the increased pore volume created by secondary porosity. The increased formation pressure may prevent further compaction of the tight formation. The increased formation pressure may improve reservoir quality and enhance the productivity of the hydrocarbon-bearing tight formation. Accordingly, carbon dioxide, which is a product of carbonate dissolution in tight formations, can serve as a geochemical indicator to track well productivity of hydrocarbon-bearing tight formations and to identify hydrocarbon sweet spots.

The trapped carbon dioxide can be geochemically categorized as originating from an inorganic source. Non-limiting examples of inorganic sources of trapped carbon dioxide include carbon dioxide generated from mantle degassing, volcanic activity, carbonate dissolution, and thermal decomposition of carbonate-based minerals. As opposed to inorganic sources, non-limiting examples of organic sources of trapped carbon dioxide include carbon dioxide generated from oil and gas, coalification, hydrocarbon destruction, and bacteria.

In some embodiments, gas retrieved from a tight formation may include carbon dioxide originating from an inorganic source. The carbon dioxide content of the gas (in terms of mole percentage) ranges from about 0% to about 100%, alternately from about 5% to about 50%, or alternately from about 9% to about 20%. For example, the gas having a carbon dioxide content of greater than about 5% can be indicative of the existence of inorganic carbon dioxide. In addition, the gas having a carbon dioxide content of greater than about 5% can be indicative of carbonate dissolution in the tight formation. For example, the gas having a carbon dioxide content ranging from about 15% to about 100% can be indicative of the existence of inorganic carbon dioxide. In addition, the gas having a carbon dioxide content ranging from about 15% to about 100% can be indicative of carbonate dissolution in the tight formation or trapping of carbon dioxide originated from mantle, or both.

In some embodiments, the inorganic carbon dioxide contained in the gas retrieved from the tight formation has a prototypical isotopic signature. As used throughout the disclosure, the carbon isotopic signature of inorganic carbon dioxide can be expressed by the delta ($\delta$) notation in units of parts per thousand (per mil, or ‰), as shown for example in equation (3):

$$\delta^{13}C = \left( \frac{\left(\frac{^{13}C}{^{12}C}\right)_{sample}}{\left(\frac{^{13}C}{^{12}C}\right)_{standard}} - 1 \right) \times 1000 \quad (3)$$

where the standard is an established reference material such as Pee Dee Belemnite (PDB). Inorganic carbon dioxide may have a $\delta^{13}C$ value of greater than about −12‰, alternately greater than about −10‰, or alternately greater than about −8‰. Such carbon isotopic signature of carbon dioxide of the gas retrieved from the tight formation is indicative of the existence of inorganic carbon dioxide and accordingly indicative of carbonate dissolution in the tight formation.

In some embodiments, certain parameters of a well such as gas flow rate and wellhead flowing pressure (WHFP) can be measured to determine the productivity of the well. If the well has a gas flow rate or WHFP, or both, greater than a predetermined value or values, hydrocarbons can be produced conventionally in a vertical well so that stimulation methods such as hydraulic fracturing and techniques such as horizontal or directional drilling are not necessary. For example, the predetermined value of the gas flow rate can be about 100 MMscf/d for megaports (having a pore throat aperture of greater than about 10 microns) and macroports (having a pore throat aperture ranging from about 2.5 microns to about 10 microns). The predetermined value of the gas flow rate can be about 10 MMscf/d for mesoports (having a pore throat aperture ranging from about 0.5 microns to about 2.5 microns). The predetermined value of the gas flow rate can be about 1 MMscf/d for microports (having a pore throat aperture ranging from about 0.1 microns to about 0.5 microns). The predetermined value of the gas flow rate can be about 0.1 MMscf/d for nanoports (having a pore throat aperture ranging from about 0.01 microns to about 0.1 microns).

Figure 1:
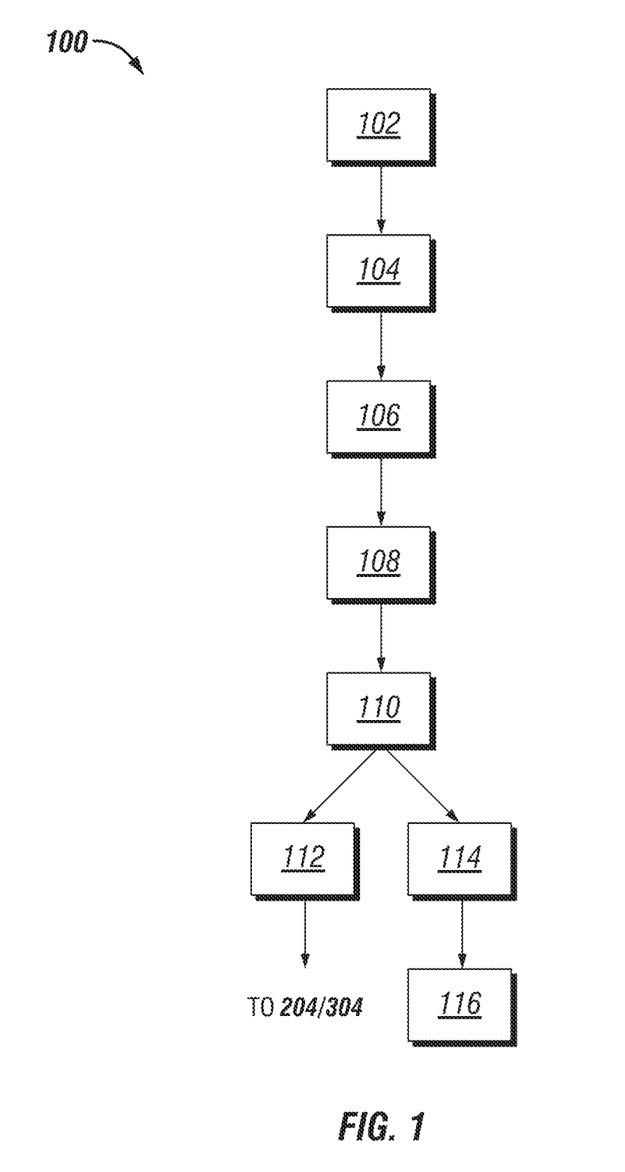
FIG. 1 is a schematic diagram showing a process for identifying a hydrocarbon sweet spot of a hydrocarbon-bearing formation in accordance with an embodiment of the disclosure.

FIG. 1 shows a process 100 for identifying a hydrocarbon sweet spot of a hydrocarbon-bearing formation in accordance with an embodiment of the disclosure.

In block 102, a prospect hydrocarbon-bearing formation is located and evaluated. The subterranean structure of the prospect formation is mapped using conventional methodologies such as seismology, geology, geochemistry, and well data. One or more target zones can be identified for formation testing and fluid sampling. Subsequently, one or more pilot wells can be drilled from the surface to the target zone. Gaseous hydrocarbon may be detected as a result of a gas show or gas kick when drilling the pilot well. However, the detection of gaseous hydrocarbon during drilling is not necessarily indicative of sustainable production. For example, the detection may result in a false positive, where the gaseous hydrocarbon is generated by a certain change in drilling conditions. The detection may result in a false negative, where gaseous hydrocarbon readings may not provide information related to the existence of petroleum. In addition, a wireline logging tool can be deployed to the target zone to measure certain petrophysical parameters such as porosity, permeability, and water saturation. However, such parameters are not necessarily indicative of sustainable production.

In block 104, a gas sample is retrieved from the pilot well. In some embodiments, wireline formation testing (WFT) can be performed by deploying a probe in the pilot well. The WFT probe reaches the target zone to retrieve a fluid sample back to the surface. The fluid sample may include gaseous components. The gaseous components may include hydrocarbons and non-hydrocarbons. In other embodiments, drill stem testing (DST) can be performed to retrieve a fluid sample of the target zone. Still in other embodiments, a fluid sample can be retrieved at the surface via a wellhead or an oil and gas separator.

In block 106, at a wellsite or offsite laboratory, conventional methodologies such as gas chromatography (GC) can be implemented to separate the gaseous components from the fluid sample retrieved in block 104. Methodologies such as GC can be implemented to analyze the composition of the separated gas sample and as a result, the carbon dioxide content (in terms of mole percentage) of the gas sample can be determined. Still in block 106, conventional methodologies such as isotope-ratio mass spectrometry (IRMS) in combination with GC can be implemented to separate carbon dioxide from the gas sample and obtain the carbon isotope signature of the separated carbon dioxide. In this manner, the $\delta^{13}C$ value of carbon dioxide can be determined. One skilled in the art may appreciate that various methodologies can be implemented to determine the carbon dioxide composition of a gas sample. One skilled in the art may also appreciate that various methodologies can be implemented to obtain the carbon isotope signature of a carbon dioxide sample.

In block 108, the geochemical origin of carbon dioxide included in the pilot well gas sample is determined using the carbon dioxide content data and the carbon isotope signature data obtained in block 106. As a non-limiting example, the carbon dioxide is determined to have an inorganic origin if the carbon isotopic signature of carbon dioxide has a $\delta^{13}C$ value of greater than about −10‰. As a non-limiting example, the carbon dioxide is determined to have an organic origin if the carbon dioxide content (in terms of mole percentage) is less than about 15% and the carbon isotopic signature of carbon dioxide has a $\delta^{13}C$ value of less than about −10‰.

In block 110, data related to the gas flow rate and WHFP are obtained in select wells. DST can be performed in select one or more pilot wells that are determined to contain inorganic carbon dioxide in block 108. In such embodiments, DST can be performed to determine parameters related to well productivity such as the gas flow rate and WHFT, which are indicative of a hydrocarbon sweet spot.

In block 112, a cutoff range of carbon dioxide content is determined. As used throughout the disclosure, the cutoff range corresponds to a productive mixture of gaseous hydrocarbon and inorganic carbon dioxide indicative of a hydrocarbon sweet spot. The carbon dioxide content data obtained in block 106 and the gas flow rate data obtained in block 110 are analyzed in conjunction to seek a positive correlation between the two parameters. The existence of a positive correlation is indicative of a hydrocarbon sweet spot in the tested pilot wells. As a non-limiting example, the minimum value of the carbon dioxide cutoff range can be set at about 9% corresponding to tested wells having threshold gas flow rates of greater than about 10 MMscf/d. As a non-limiting example, the maximum value of the carbon dioxide cutoff range can be set at about 20% due to the diminishing economic value of the produced hydrocarbon gas as the carbon dioxide content increases. One skilled in the art would recognize that the carbon dioxide cutoff range and the threshold gas flow rate may vary depending on the geographic location, well testing results, the production strategy of hydrocarbon producers, and the local, regional, or worldwide natural gas market.

Alternately, in block 114, a hydrocarbon sweet spot can be identified. The gas flow rate or WHFP, or both, obtained in block 110 can be compared with a predetermined value or values. As a non-limiting example, a hydrocarbon sweet spot is identified if the gas flow rate obtained in block 110 is greater than a predetermined value of about 10 MMscf/d. One skilled in the art may recognize that the predetermined gas flow rate may vary depending on the geographic location, well testing results, the production strategy of hydrocarbon producers, and the local, regional, or worldwide natural gas market.

In block 116, well completion is conducted at the hydrocarbon sweet spot identified in block 114. Hydrocarbons can be produced conventionally in a vertical well so that stimulation methods such as hydraulic fracturing, and methods such as horizontal or directional drilling are not necessary. Alternately, if the gas flow rate obtained in block 110 is less than a predetermined value shown for example in block 114, stimulation methods such as hydraulic fracturing can be implemented to the well, with or without horizontal or directional drilling. Subsequently, similar to the process shown in blocks 110 and 114, data related to the gas flow rate or WHFP, or both, of the stimulated well can be obtained to determine whether the stimulated well is productive. If so, well completion is conducted at the stimulated well and hydrocarbons can be produced.

Figure 2:
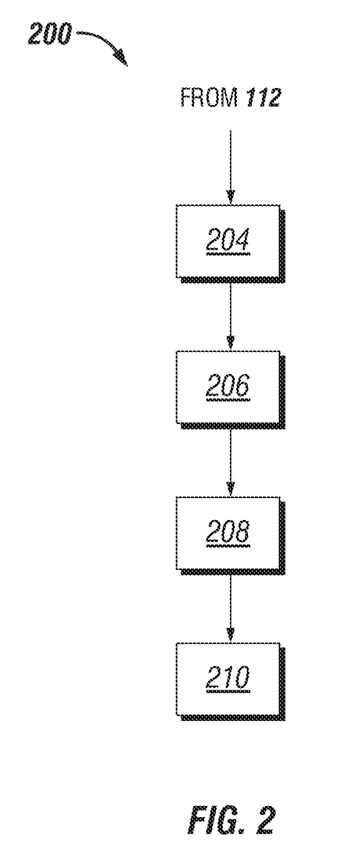
FIG. 2 is a schematic diagram showing a process for identifying a hydrocarbon sweet spot of a hydrocarbon-bearing formation in accordance with an embodiment of the disclosure.

FIG. 2 shows a process 200 for identifying a hydrocarbon sweet spot of a hydrocarbon-bearing formation in accordance with an embodiment of the disclosure.

In block 204, a gas sample is retrieved from an appraisal or production well of a prospect formation as shown for example in block 102. In some embodiments, WFT can be performed by deploying a probe in the appraisal or production well. The WFT probe reaches the target zone to retrieve a fluid sample back to the surface. The fluid sample may include gaseous components. The gaseous components may include hydrocarbons and non-hydrocarbons.

In block 206, at a wellsite or offsite laboratory, conventional methodologies such as GC can be implemented to separate the gaseous components from the fluid sample retrieved in block 204. Methodologies such as GC can be implemented to analyze the composition of the separated gas sample and as a result, the carbon dioxide content (in terms of mole percentage) of the gas sample can be determined. Optionally, conventional methodologies such as IRMS in combination with GC can be implemented to separate carbon dioxide from the gas sample and obtain the carbon isotope signature of the separated carbon dioxide. In this manner, the $\delta^{13}C$ value of carbon dioxide can be determined. One skilled in the art may appreciate that various methodologies can be implemented to determine the carbon dioxide composition of a gas sample. One skilled in the art may also appreciate that various methodologies can be implemented to obtain the carbon isotope signature of a carbon dioxide sample.

In block 208, a hydrocarbon sweet spot is identified. The carbon dioxide content data obtained in block 206 are compared with the carbon dioxide cutoff range determined in block 112. Because the prospect formation is determined in block 112 to have a positive correlation between the carbon dioxide content and the gas flow rate indicative of a hydrocarbon sweet spot, it is not necessary to conduct carbon isotope analysis or conduct DST to obtain the gas flow rate and WHFP. As a non-limiting example, a hydrocarbon sweet spot is identified if the carbon dioxide content of the gas sample in block 206 falls in the example carbon dioxide cutoff range (determined in block 112) of from about 9% to about 20%.

In block 210, well completion is conducted at the hydrocarbon sweet spot identified in block 208. The identification of a hydrocarbon sweet spot may enable the conventional production of hydrocarbons in a vertical well without the use of stimulation methods such as hydraulic fracturing or techniques such as horizontal or directional drilling.

Figure 3:
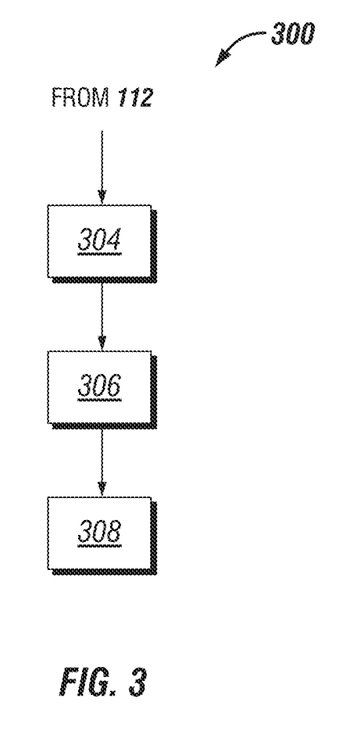
FIG. 3 is a schematic diagram showing a process for identifying a hydrocarbon sweet spot of a hydrocarbon-bearing formation in accordance with an embodiment of the disclosure.

FIG. 3 shows a process 300 for identifying a hydrocarbon sweet spot of a hydrocarbon-bearing formation in accordance with an embodiment of the disclosure.

In block 304, carbon dioxide content (in terms of mole percentage) of a gas sample can be determined in situ utilizing downhole fluid analysis (DFA). DFA can use a WFT fluid analyzer module positioned at the target zone to retrieve a fluid sample via the WFT flowline. The WFT fluid analyzer can include an optical spectrometer to obtain compositional data, including the carbon dioxide content. One skilled in the art may appreciate that various methodologies can be implemented to determine the carbon dioxide composition of a fluid sample in situ.

In block 306, a hydrocarbon sweet spot is identified. The carbon dioxide content data obtained in block 304 are compared with the carbon dioxide cutoff range determined in block 112. Because the prospect formation is determined in block 112 to have a positive correlation between the carbon dioxide content and the gas flow rate indicative of a hydrocarbon sweet spot, it is not necessary to conduct carbon isotope analysis or conduct DST to obtain the gas flow rate and WHFP. As a non-limiting example, a hydrocarbon sweet spot is identified if the carbon dioxide content of the gas sample in block 304 falls in the example carbon dioxide cutoff range (determined in block 112) of from about 9% to about 20%.

In block 308, well completion is conducted at the hydrocarbon sweet spot identified in block 306. As noted in the disclosure, in such instances hydrocarbons can be produced conventionally in a vertical well so that stimulation methods such as hydraulic fracturing and techniques such as horizontal or directional drilling are not necessary.

EXAMPLES

The disclosure is illustrated by the following examples, which are presented for illustrative purposes only, and are not intended as limiting the scope of the invention which is defined by the appended claims.

Example 1

Two gaseous hydrocarbon prospect formations, Prospect A and Prospect B, were identified. Prospect A and Prospect B are about 200 kilometers apart. Prospect A and Prospect B include shale formations as organic-rich source rocks and also include sand formations as potential gaseous hydrocarbon-bearing formations. Prospect A is a gas and condensate discovery. Prospect B is a methane-dominated dry gas discovery.

Example 2

Pyrolysis experiments were conducted on multiple source rocks retrieved from Prospect A and Prospect B. Kerogen concentrate was separated from the source rock in each experiment to undergo pyrolysis. Carbon dioxide was produced during each kerogen concentrate pyrolysis experiment and the produced carbon dioxide was collected. The carbon isotopic signature of the produced carbon dioxide was determined using IRMS. The $\delta^{13}C$ values of the produced carbon dioxide were measured to be about −30‰. The carbon isotopic signature of the produced carbon dioxide confirmed that the produced carbon dioxide from kerogen has an organic origin, that is, the produced carbon dioxide is organic carbon dioxide.

Example 3

Multiple gas samples were retrieved via WFT or DST, or both, from various target zones in select wells of Prospect A and Prospect B. The carbon dioxide content of each gas sample was determined using GC. Also, the carbon isotopic signature of carbon dioxide separated from each gas sample was determined using IRMS in combination with GC. The results are plotted in FIG. 4.

Figure 4:
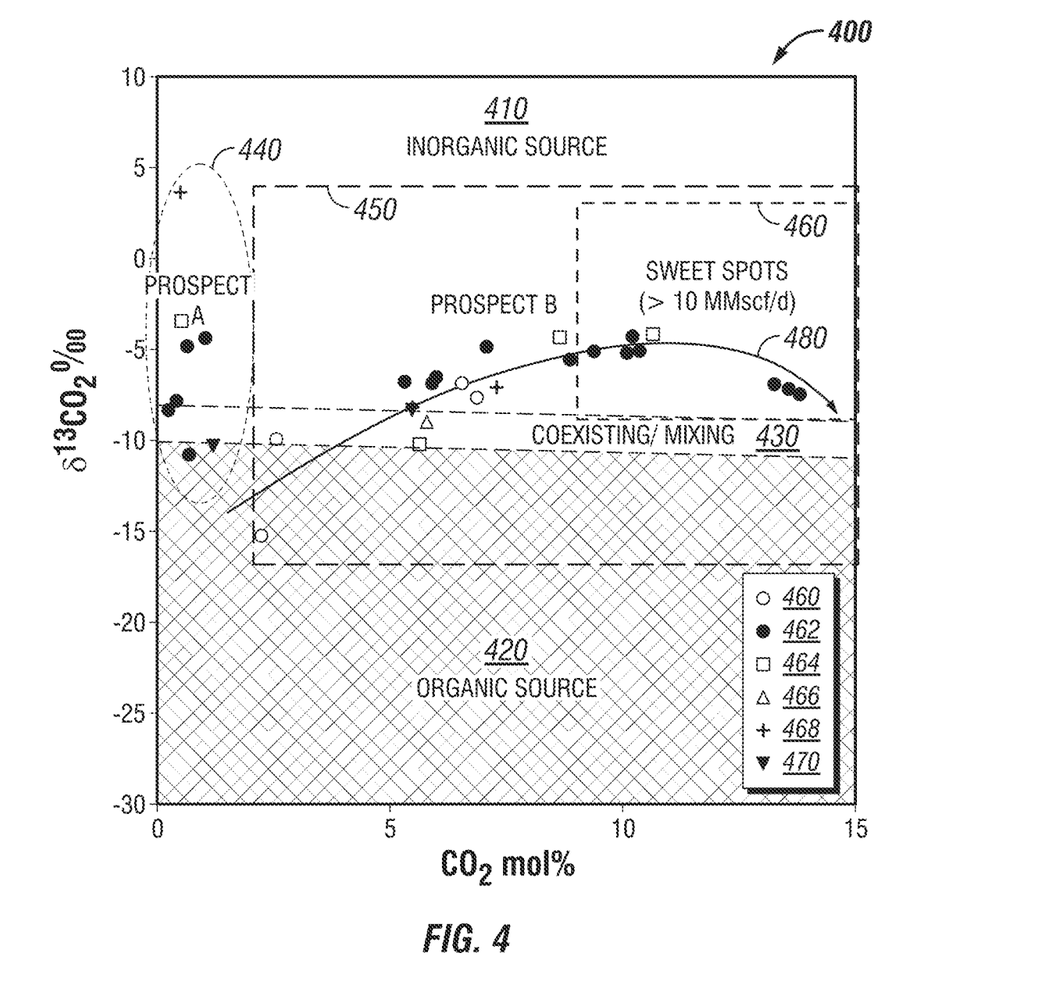
FIG. 4 is a graphical representation showing certain geochemical parameters of carbon dioxide retrieved from multiple target zones in select wells of two prospect formations in accordance with an embodiment of the disclosure.

FIG. 4 is a graphical representation 400 showing certain geochemical parameters of carbon dioxide retrieved from multiple target zones in select wells of Prospect A and Prospect B in accordance with an embodiment of the disclosure. The horizontal axis represents the carbon dioxide content of a gas sample in mole percentage (mol %). The vertical axis represents the $\delta^{13}C$ value of carbon dioxide separated from a gas sample in ‰. The following zones are shown in FIG. 4: zone 410 represents inorganic carbon dioxide; zone 420 represents organic carbon dioxide; and zone 430 represents coexisting inorganic carbon dioxide and organic carbon dioxide. The following areas are shown in FIG. 4: area 440 includes gas samples retrieved from target zones of Prospect A; area 450 includes gas samples retrieved from target zones of Prospect B; and area 460 includes gas samples retrieved from certain target zones of Prospect B, which correspond to sweet spots having a gas flow rate of greater than about 10 MMscf/d. The following points are shown in FIG. 4: blank circular points 460 represent gas samples retrieved from target zones having Shale A; filled circular points 462 represent gas samples retrieved from target zones having Sand A; square points 464 represent gas samples retrieved from target zones having Sand B; triangular points 466 represent gas samples retrieved from target zones having Shale B; cross-shaped points 468 represent gas samples retrieved from target zones having Sand C; and reverse-triangular points 470 represent gas samples retrieved from target zones having Sand D. Shale A and Shale B are different types of shale where "A" and "B" are arbitrarily assigned and are merely intended to differentiate between the two types of shale. Sand A, Sand B, Sand C, and Sand D are different types of sand where "A," "B," "C," and "D" are arbitrarily assigned and are merely intended to differentiate between the four types of sand. As also shown in FIG. 4, regression curve 480 represents carbonate dissolution in tight formations.

The results depicted in FIG. 4 show that the majority of gas samples retrieved from target zones in Prospect A and Prospect B have inorganic carbon dioxide. As shown in FIG. 4, the gas samples have a carbon dioxide content ranging from 0‰ to 14% and a $\delta^{13}C$ value ranging from −16‰ to 4‰. The majority of datapoints in area 440 corresponding to gas samples retrieved from target zones in Prospect A are located in zone 410 or zone 430 indicative of inorganic carbon dioxide. The majority of datapoints in area 450 corresponding to gas samples retrieved from target zones in Prospect B are located in zone 410 or zone 430 indicative of inorganic carbon dioxide. Datapoints in area 460 are located in zone 410 indicative of inorganic carbon dioxide and indicative of sweet spots.

Example 4

A noble gas study was conducted on eight gas samples retrieved from one or more target zones in Prospect B. Helium isotopic signatures of each gas sample was obtained using IRMS to determine an R/Ra value as shown for example in equation (4):

$$R/Ra = (^{3}He/^{4}He)_{sample}/(^{3}He/^{4}He)_{air} \quad (4)$$

where R is the ratio of $^{3}He$ to $^{4}He$ in the sample and Ra is the ratio of $^{3}He$ to $^{4}He$ in present day atmosphere. An R/Ra value greater than about 2.0 is indicative of carbon dioxide originating from magma or from the thermal decomposition of carbonates by magmatic intrusion. An R/Ra value ranging from about 1.0 to about 2.0 is indicative of carbon dioxide originating from a crustal-mantle transition zone. An R/Ra value less than about 1.0 is indicative of carbon dioxide originating from a crustal origin, such as from carbonate dissolution.

The R/Ra values obtained from the eight gas samples ranged from about 0.02 to about 0.045, confirming that the inorganic carbon dioxide identified in these gas samples were not generated by mantle degassing or volcanic activity.

Example 5

Petrographic analysis was conducted on four samples retrieved from multiple locations of a select well of Prospect B. DST was conducted to measure the gas flow rate of the select well, which was greater than about 10 MMscf/d. The results are shown in FIGS. 5A-H.

Figure 5A:
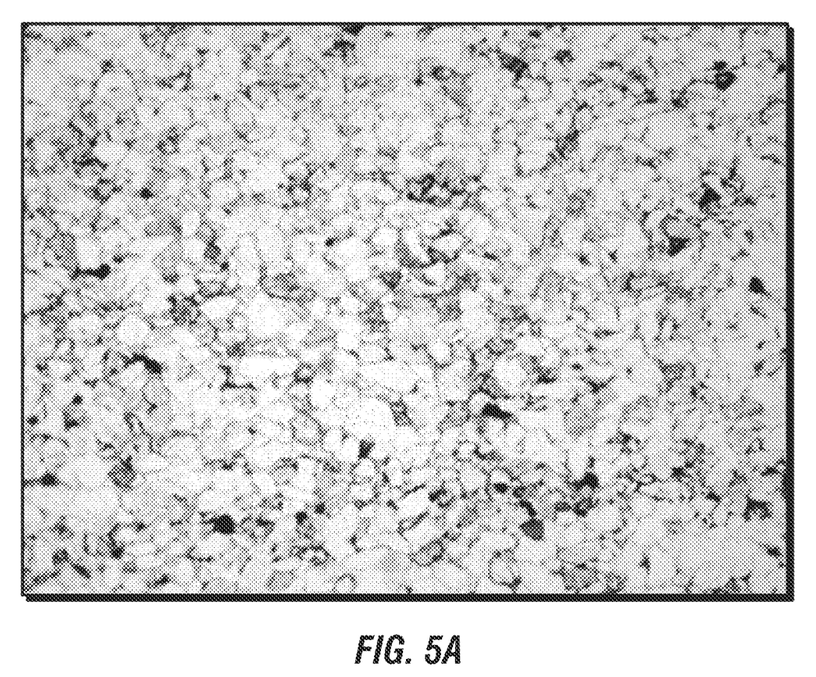
FIG. 5A is a photographic representation showing petrographic analysis of one of four sandstone samples retrieved from a select well of a prospect formation in accordance with an embodiment of the disclosure.
Figure 5B:
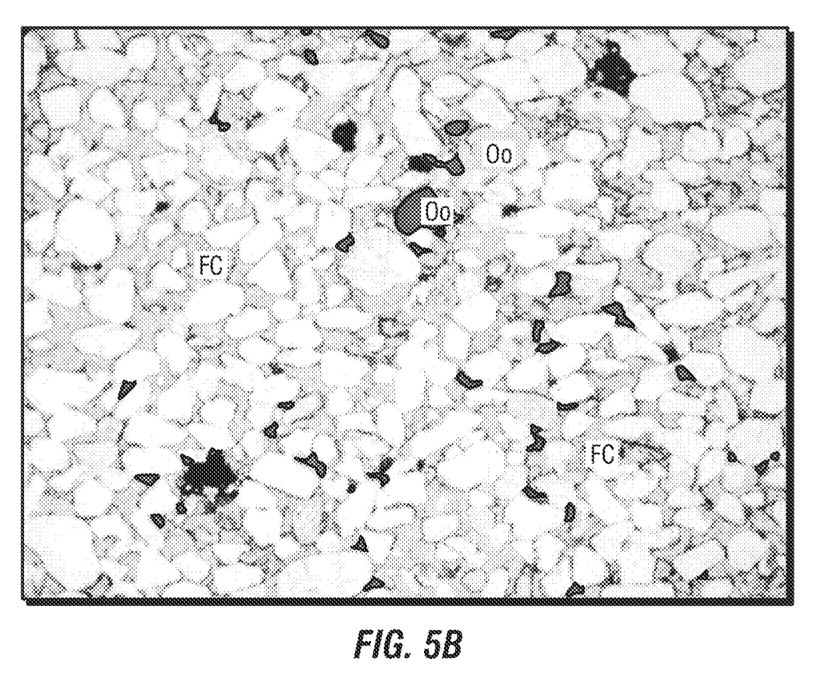
FIG. 5B is a photographic representation showing petrographic analysis of one of four sandstone samples retrieved from a select well of a prospect formation in accordance with an embodiment of the disclosure.
Figure 5C:
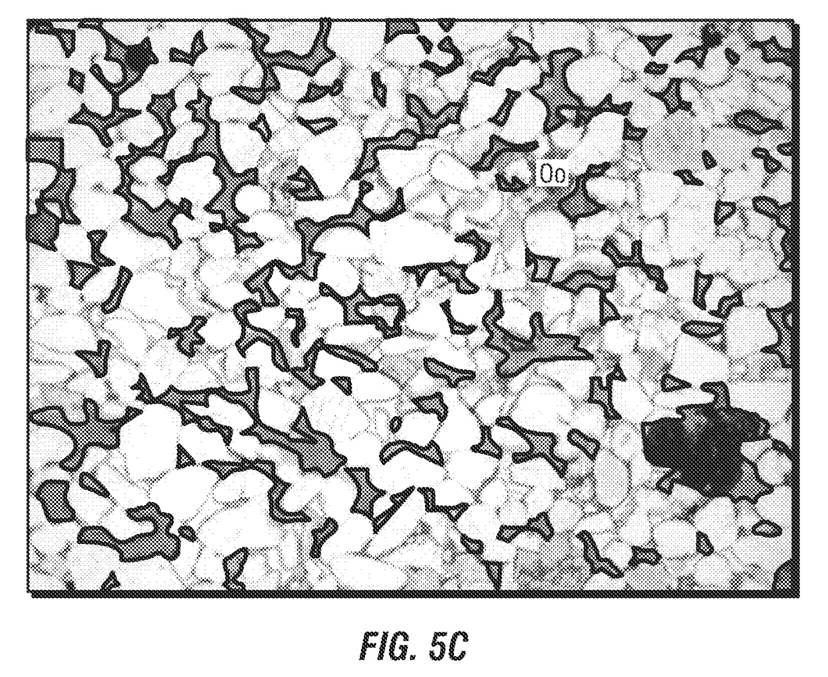
FIG. 5C is a photographic representation showing petrographic analysis of one of four sandstone samples retrieved from a select well of a prospect formation in accordance with an embodiment of the disclosure.
Figure 5D:
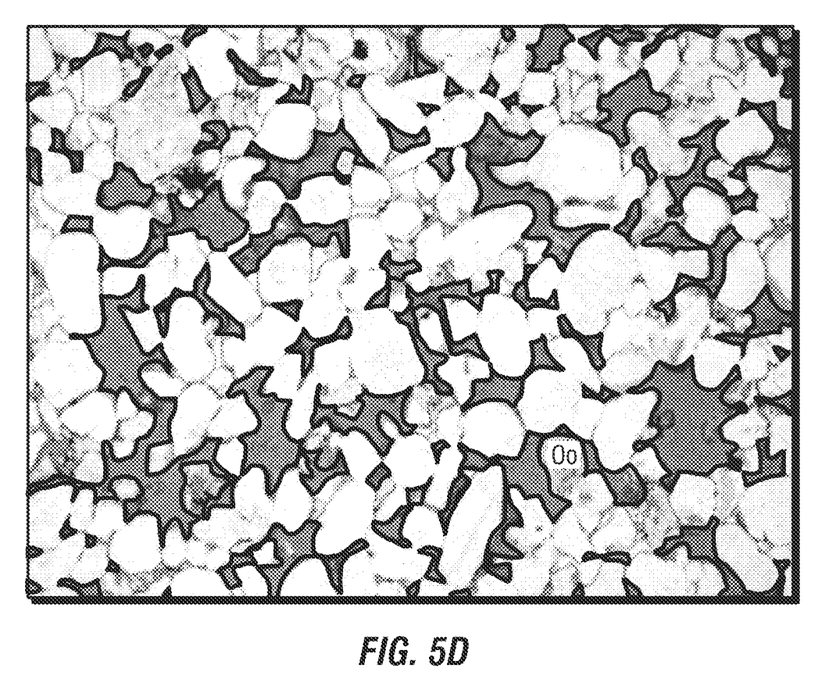
FIG. 5D is a photographic representation showing petrographic analysis of one of four sandstone samples retrieved from a select well of a prospect formation in accordance with an embodiment of the disclosure.
Figure 5E:
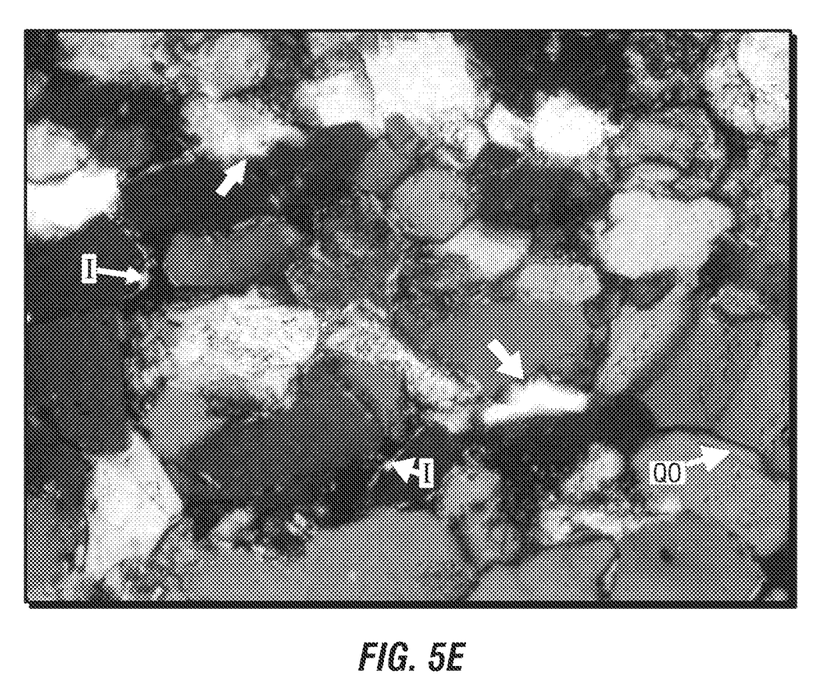
FIGS. 5E-H are enlarged photographic representations of select areas in FIGS. 5A-D, respectively.
Figure 5F:
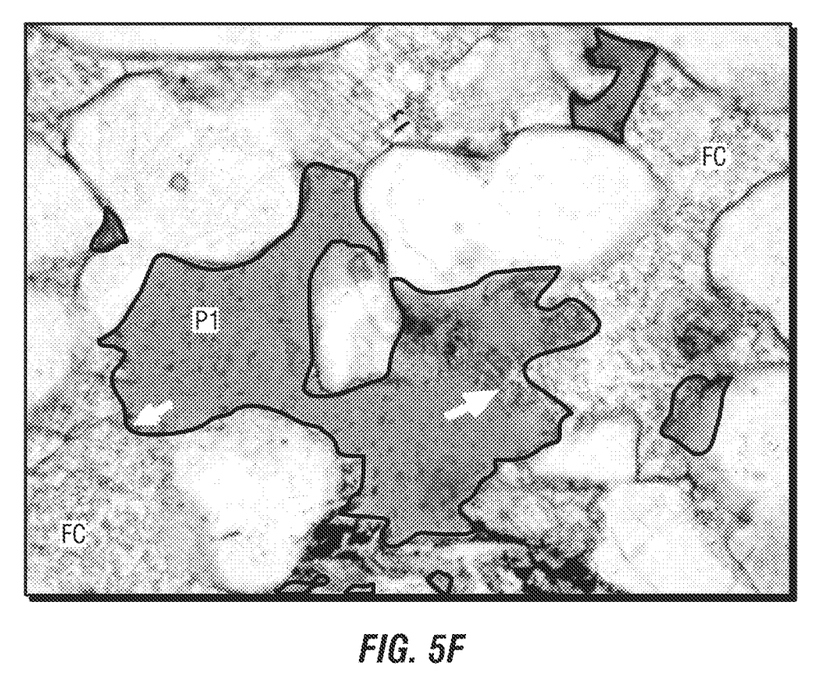
Figure 5G:
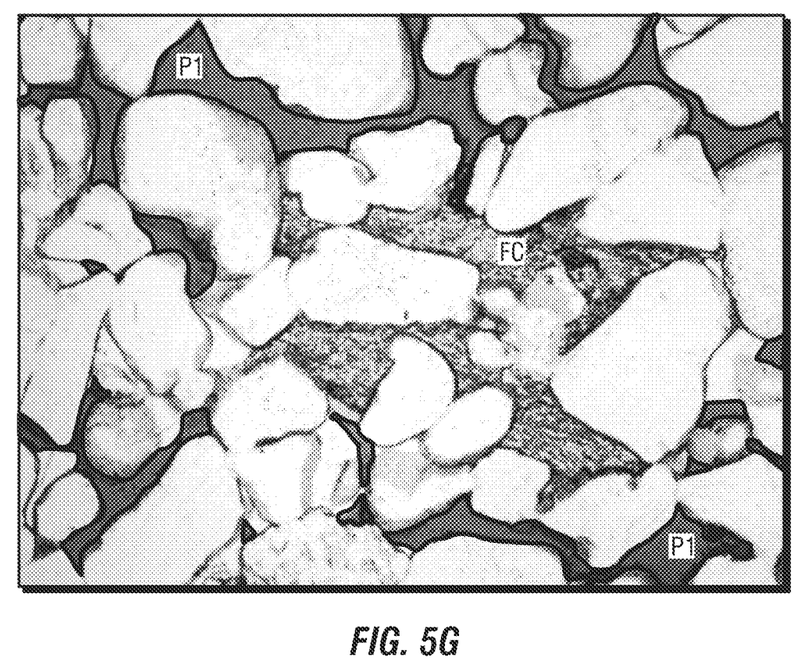
Figure 5H:
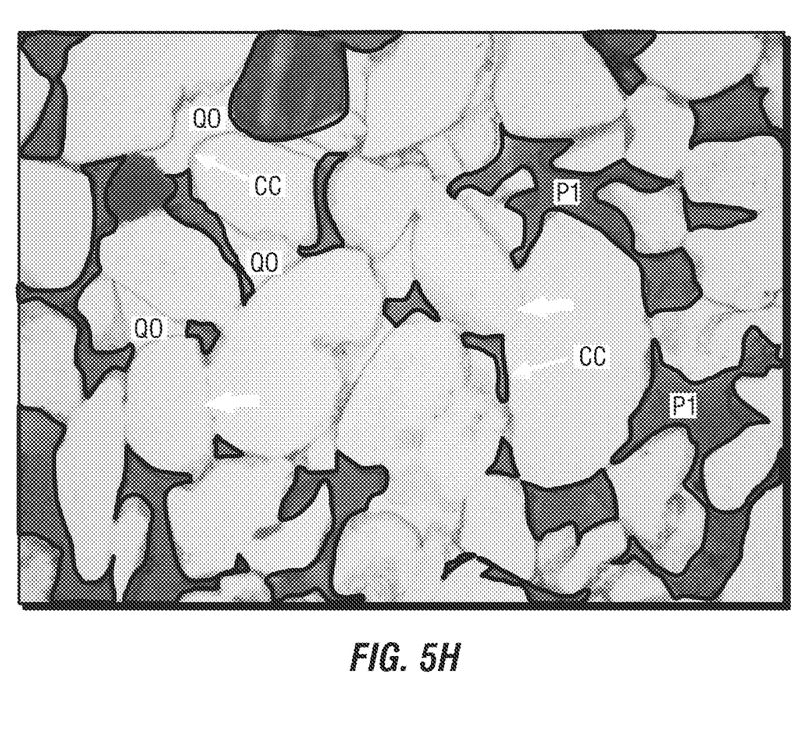

FIGS. 5A-H are photographic representations showing petrographic analyses of four samples retrieved from a select well in Prospect B in accordance with an embodiment of the disclosure. FIG. 5A shows petrographic analysis of a sandstone sample (Sample A having porosity of 2.4% and permeability of less than 0.01 mD) retrieved from a location in a non-productive zone. FIG. 5B shows petrographic analysis of a sandstone sample (Sample B having porosity of 7.6% and permeability of 0.3 mD) retrieved from a location in a non-productive zone proximate to the interface between the non-productive zone and a productive zone. FIG. 5C shows petrographic analysis of a sandstone sample (Sample C having porosity of 17.1% and permeability of 785 mD) retrieved from a location in a productive zone. FIG. 5D shows petrographic analysis of a sandstone sample (Sample D having porosity of 24.3% and permeability of 2,182 mD) retrieved from another location in the productive zone. FIGS. 5E-G are enlarged images of select areas shown in FIGS. 5A-D, respectively. As shown in FIGS. 5A-H, Oo represents a clay ooid, FC represents a siderite cement, CC represents a calcite cement, I represents an illite cement, QO represents a quartz overgrowth, and P1 represents an oversized preserved intergranular pore. The dark looped curves in FIGS. 5B-D and F-H indicate example sites of intergranular pores. The bold arrows in FIG. 5E show example sites of sutured grain contacts. The bold arrows in FIG. 5F show example etching sites of the siderite cement (FC). The bold arrows in FIG. 5H show example delimitation sites of the quartz overgrowth (QO) by abundant detrital clay grain coatings.

The petrographic analysis results shown in FIGS. 5A-H confirmed that inorganic carbon dioxide was generated from the dissolution of carbonate-based cements in tight formations, resulting in increasing formation pressure and improved reservoir quality. As shown in FIGS. 5A-H, carbonate cementation is most frequently observed in Sample A, followed by Sample B, followed by Sample C, and followed by Sample D. Conversely, oversized preserved intergranular pores (corresponding to P1) are most frequently observed in Sample D, followed by Sample C, followed by Sample B, and followed by Sample A. These intergranular pores are formed by substantial carbonate dissolution. For example, FIG. 5F shows possible etching of siderite (FC) proximate to an oversized intergranular pore (P1), indicated by the bold arrows. The etching corresponding to the carbonate dissolution of siderite resulted in an increase in porosity. Upon dissolution, inorganic carbon dioxide is generated and can be trapped in the intergranular pore.

Example 6

Multiple gas samples were retrieved via DST from various target zones in select wells of Prospect A and Prospect B. The carbon dioxide content of each gas sample was determined using GC. Also, the gas flow rate and WHFP were measured via DST in select wells of Prospect A and Prospect B. The results are plotted in FIG. 6.

Figure 6:
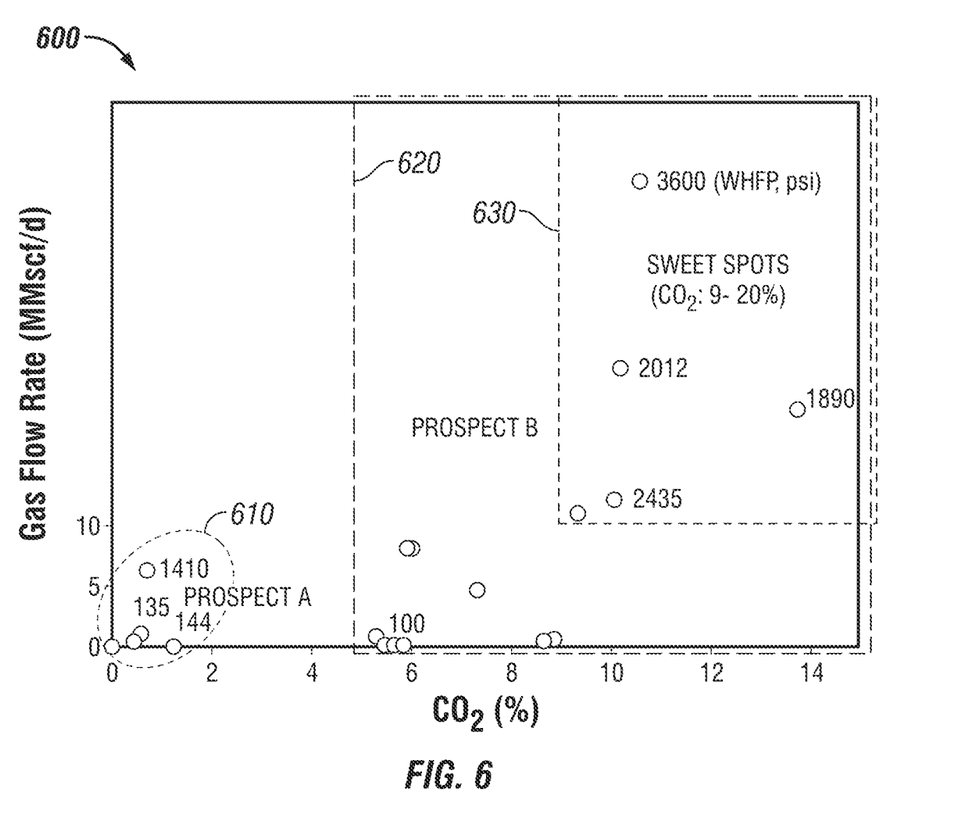
FIG. 6 is a graphical representation showing certain geochemical parameters of carbon dioxide retrieved from multiple target zones in select wells of two prospect formations and certain well productivity parameters of the select wells of the two prospect formations in accordance with an embodiment of the disclosure.

FIG. 6 is a graphical representation 600 showing certain geochemical parameters of carbon dioxide retrieved from multiple target zones in select wells of Prospect A and Prospect B and certain well productivity parameters of the select wells of Prospect A and Prospect B in accordance with an embodiment of the disclosure. The horizontal axis represents the carbon dioxide content of a gas sample in mol %. The vertical axis represents the DST gas flow rate of a select well in MMscf/d. The following areas are shown in FIG. 6: area 610 includes gas samples retrieved from target zones of Prospect A and DST gas flow rates of Prospect A; area 620 includes gas samples retrieved from target zones of Prospect B and DST gas flow rates of Prospect B; and area 630 includes gas samples retrieved from target zones of Prospect B and DST gas flow rates of Prospect B, which correspond to sweet spots having a gas flow rate of greater than 10 MMscf/d. The numerals proximate to filled circular points represent WHFP values in pounds per square inch (psi).

The results show that Prospect A was not productive. The results also show that each datapoint corresponding to a hydrocarbon sweet spot (that is, each datapoint having a gas flow rate of greater than 10 MMscf/d) has a carbon dioxide content of greater than about 9%. The results also show a positive correlation between the carbon dioxide content and the gas flow rate. Accordingly, in some embodiments, a minimum value of a carbon dioxide cutoff range can be set at about 9%.

Example 7

The carbon dioxide cutoff range determined in Example 6 was blind tested on various target zones in select wells of Prospect B. The results are shown in Table 1. The carbon dioxide content was determined via WFT or DST, or both. As shown in Table 1, only the DST examples provided gas flow rate data. Certain DST examples included a second gas flow rate data which was measured after undergoing well stimulation such as hydraulic fracturing. Predictions were based on the carbon dioxide cutoff range of greater than about 9%. Actual conclusions were previously determined using conventional methods of formation evaluation such as wireline log analysis.

TABLE 1

RESULTS OF BLIND TESTING OF CARBON DIOXIDE CUTOFF RANGE IN VARIOUS TARGET ZONES

| Well | Reservoir Type | $CO_2$ content (mol %) | Sampling Method | Gas Flow Rate (MMscf/d) | Post-Frac Gas Flow Rate (MMscf/d) | Sweet Spot Prediction Based on $CO_2$ Cutoff Range | Actual Conclusion |
|---|---|---|---|---|---|---|---|
| J3 | Sand A | 5.91 | DST | 8 | | Not Productive | Producible |
| J3 | Sand A | 5.97 | DST | 8 | | Not Productive | Producible |
| J3 | Sand A | 6.01 | DST | 8 | | Not Productive | Producible |
| J3 | Sand A | 5.99 | DST | 8 | | Not Productive | Producible |
| J3 | Sand A | 5.97 | DST | 8 | | Not Productive | Producible |
| J3 | Sand A | 6.01 | DST | 8 | | Not Productive | Producible |
| S2 | Sand A | 9.34 | DST | 11 | | Productive | Productive |
| S2 | Sand A | 9.34 | DST | 11 | | Productive | Productive |
| S3 | Sand A | 9.29 | DST | 3.7 | 20 | Productive | Productive |
| S3 | Sand A | 9.32 | DST | 3.7 | 20 | Productive | Productive |
| S3 | Sand A | 9.18 | DST | 3.7 | 20 | Productive | Productive |
| S3 | Sand C | 7.30 | DST | 4.5 | | Not Productive | Not Productive |
| S3 | Sand C | 7.23 | DST | 4.5 | | Not Productive | Not Productive |
| S3 | Sand C | 7.67 | DST | 4.5 | | Not Productive | Not Productive |
| S3 | Sand C | 7.67 | DST | 4.5 | | Not Productive | Not Productive |
| S3 | Sand B | 6.90 | DST | 4.5 | | Not Productive | Not Productive |
| S3 | Sand B | 6.82 | DST | 4.5 | | Not Productive | Not Productive |
| S4 | Sand A | 8.85 | DST | 0.5 | 2 | Not Productive | Not Productive |
| U3 | Sand A | 10.03 | DST | >10 | | Productive | Productive |
| J1 | Sand A | 9.36 | WFT | | | Productive | Productive |
| J1 | Sand A | 9.4 | WFT | | | Productive | Productive |
| J2 | Sand A | 10.26 | WFT | | | Productive | Productive |
| U1 | Sand A | 9.64 | WFT | | | Productive | Productive |
| U1 | Sand A | 8.58 | WFT | | | Not Productive | Productive |
| U2 | Sand A | 11.25 | WFT | | | Productive | Productive |
| U2 | Sand A | 10.84 | WFT | | | Productive | Productive |
| S1 | Sand A | 11.33 | WFT | | | Productive | Productive |
| S1 | Sand A | 11.33 | WFT | | | Productive | Productive |
| S1 | Sand A | 11.52 | WFT | | | Productive | Productive |
| S1 | Sand A | 11.47 | WFT | | | Productive | Productive |
| S5 | Sand A | 9.08 | WFT | | | Productive | Not Productive |
| S5 | Sand A | 9.02 | WFT | | | Productive | Not Productive |
| S5 | Sand B-C | 12.4 | WFT | | | Productive | Productive |
| U3 | Sand A | 8.25 | WFT | | | Not Productive | Not Productive |

The results in Table 1 indicate that sweet spot predictions based on the carbon dioxide cutoff range and actual conclusions are in general agreement. As shown in Table 1, DST target zones having carbon dioxide content of greater than about 9% were predicted and determined to be productive (that is, the gas flow rate is greater than about 10 MMscf/d), either with or without well stimulation. DST target zones having carbon dioxide content of less than about 9% were predicted and determined to be non-productive (that is, the gas flow rate is less than about 10 MMscf/d). WFT target zones having carbon dioxide content of greater than about 9% were predicted and determined to be productive. WFT target zones having carbon dioxide content of less than about 9% were predicted and determined to be non-productive.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method for evaluating a hydrocarbon-bearing formation, the method comprising the step of:
    identifying a hydrocarbon sweet spot comprising the steps of:
        determining a carbon dioxide content of a gas sample retrieved from the hydrocarbon-bearing formation;
        determining an isotopic signature of carbon dioxide of the gas sample, and
        obtaining a gas flow rate of the hydrocarbon-bearing formation.

2. The method of claim 1, where the carbon dioxide content of the gas sample has a mole percentage ranging from 9 percent to 20 percent.

3. The method of claim 1, where the isotopic signature of carbon dioxide of the gas sample has a $\delta^{13}C$ value greater than −10 per mil.

4. The method of claim 1, where the gas flow rate is greater than 10 million standard cubic feet per day.

5. The method of claim 1, where the hydrocarbon-bearing formation is a tight formation.

6. The method of claim 1, where the gas sample is retrieved via at least one of: wireline formation testing and drill stem testing.

7. The method of claim 1, the identifying step further comprising the step of:
    determining a cutoff range of the carbon dioxide content corresponding to the hydrocarbon sweet spot.

8. The method of claim 7, where the cutoff range has a mole percentage ranging from 9 percent to 20 percent.

* * * * *